US012751651B2

(12) United States Patent
Go

(10) Patent No.: US 12,751,651 B2
(45) Date of Patent: Oct. 6, 2026

(54) MEASUREMENT DEVICE FOR A MEASUREMENT TARGET COMPONENT CONTAINED IN A LIQUID SAMPLE

(71) Applicant: ARKRAY, Inc., Kyoto (JP)

(72) Inventor: Gai Go, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 480 days.

(21) Appl. No.: 18/453,824

(22) Filed: Aug. 22, 2023

(65) Prior Publication Data

US 2024/0074679 A1 Mar. 7, 2024

(30) Foreign Application Priority Data

Sep. 2, 2022 (JP) ................................ 2022-140321

(51) Int. Cl.
*A61B 5/145* (2006.01)

(52) U.S. Cl.
CPC .... *A61B 5/14532* (2013.01); *A61B 2562/227* (2013.01)

(58) Field of Classification Search
CPC .......... A61B 2562/227; A61B 5/14532; G01N 27/3273; G01N 33/4875; G01N 33/492; H01R 13/2407
See application file for complete search history.

(56) References Cited

U.S. PATENT DOCUMENTS

2002/0037667 A1* 3/2002 Oguchi ................ G06K 7/0021 439/630
2006/0121759 A1 6/2006 Kasai
2007/0249921 A1* 10/2007 Groll .................. G01N 27/3273 600/347

(Continued)

FOREIGN PATENT DOCUMENTS

JP 2019-215343 A 12/2019
WO 2004/112200 A1 12/2004
WO 2007/121966 A1 11/2007

OTHER PUBLICATIONS

Extended European Search Report issued in the corresponding Application No. 23193179.1, dated Dec. 20, 2023.

(Continued)

*Primary Examiner* — Abdullah A Riyami
*Assistant Examiner* — Thang H Nguyen
(74) *Attorney, Agent, or Firm* — Morgan, Lewis & Bockius LLP

(57) ABSTRACT

A measurement device including an insertion port into which a sensor is inserted and plural terminals that contacts the sensor, wherein the terminals slide on a contact surface of the sensor at which a measurement target component is measured, a first electrode group located on a rear end side and a second electrode group located on a farther distal end side are provided on the contact surface, the plural terminals receive normal forces from the contact surface and include a first terminal group that contacts the first electrode group on a side closer to the insertion port than a side on which a second terminal group contacts the second electrode group, and a sum of normal forces that the first terminal group receives from the contact surface is smaller than a sum of normal forces that the second terminal group receives from the contact surface.

12 Claims, 12 Drawing Sheets

(56) References Cited

U.S. PATENT DOCUMENTS

| | | | | |
|---|---|---|---|---|
| 2007/0266871 | A1* | 11/2007 | Wegner | B01L 3/502707<br>101/395 |
| 2010/0276286 | A1* | 11/2010 | Nishimura | G01N 27/3273<br>204/403.02 |
| 2013/0175184 | A1 | 7/2013 | Iyengar et al. | |
| 2018/0172616 | A1 | 6/2018 | Neel et al. | |
| 2019/0376921 | A1* | 12/2019 | Gokuden | G01N 27/283 |

OTHER PUBLICATIONS

Office Action issued in the corresponding EP Application No. 23193179.1, dated Oct. 9, 2024.

Office Action issued in corresponding Japanese Patent Application No. 2022-140321, dated Jun. 2, 2026.

* cited by examiner

MEASUREMENT DEVICE FOR A MEASUREMENT TARGET COMPONENT CONTAINED IN A LIQUID SAMPLE

CROSS-REFERENCE TO RELATED APPLICATION

This application claims priority under 35 USC 119 from Japanese Patent Application No. 2022-140321, filed on Sep. 2, 2022, the disclosure of which is incorporated by reference herein.

BACKGROUND

Technical Field

The present invention relates to a measurement device that measures a measurement target component contained in a liquid sample attached to a sensor in a state in which the sensor is inserted.

Related Art

Blood glucose measurement systems using a disposable sensor and a self blood glucose measurement device (hereinafter, measurement device) are widely used. In such a system, a sensor is inserted into the measurement device, and the two of these are electrically connected. As a specific example of such connection, there is connection in which a swing-side terminal of a connector of a measurement device is brought into contact with a conductive terminal portion continuously extending from a measurement electrode of a sensor to be electrically connected as in a technique described in WO 2004/112200 A1.

In recent years, it is required to obtain not only blood glucose but also second and third information such as hematocrit by one sensor. Therefore, there is a need to increase the number of conductive terminal portions in a sensor. Therefore, a measurement device including a first conductive portion group (connector internal swing-side metal terminal group) extending in an insertion direction of a sensor and a second conductive portion group (connector group) extending in a direction intersecting the insertion direction of the sensor has been proposed as in a technique described in Japanese Patent Application Laid-Open (JP-A) No. 2019-215343. Moreover, a measurement device including two rows of conductive portion groups in the longitudinal direction and a test strip corresponding thereto have been also proposed as in a technique described in US 2018/0172616 A1.

On the other hand, as a technique for reducing friction between a measurement device and a test piece, a technique in which the shape of an arm portion of a connector is devised has been disclosed as described in WO 2007/121966 A1.

In the related art as described above, friction inevitably occurs between a terminal included on a measurement device side and a sensor surface from an insertion start position to an insertion completion position in a case in which a sensor is inserted into the measurement device. Wiring on the sensor surface and plating on a terminal surface have sometimes been damaged by this friction.

SUMMARY

A first aspect of the present disclosure is a measurement device including an insertion port into which a sensor is inserted and plural terminals that contact the sensor inside the insertion port, wherein the terminals slide on a contact surface at which the sensor faces the terminals during a period from start of insertion to completion of insertion of the sensor, and a measurement target component contained in a liquid sample attached to the sensor is measured in a state in which the sensor is inserted into the insertion port, a first electrode group located on a rear end side in an insertion direction and a second electrode group located on a farther distal end side as compared with the first electrode group are provided on the contact surface that contacts the terminals in an insertion region of the sensor, which is a portion inserted into the insertion port, the plural terminals receive normal forces from the contact surface by pressing the contact surface, and include a first terminal group that contacts the first electrode group on a side closer to the insertion port than a side on which a second terminal group contacts the second electrode group, and a sum of normal forces that the first terminal group receives from the contact surface in a state in which the sensor is inserted into the insertion port is smaller than a sum of normal forces that the second terminal group receives from the contact surface.

According to an embodiment of the present application, normal forces that terminals receive from a contact surface of a sensor can be reduced.

BRIEF DESCRIPTION OF THE DRAWINGS

Exemplary embodiments will be described in detail based on the following figures, wherein.

DETAILED DESCRIPTION

Figure 1:
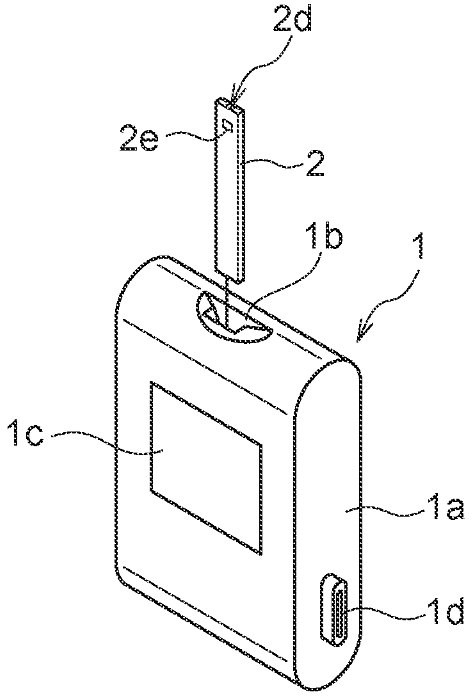
FIG. 1 is a perspective view schematically illustrating appearance of a measurement device of an exemplary embodiment.

Hereinafter, an example of an exemplary embodiment according to the present disclosure will be described with reference to the drawings. Note that, in the drawings, the same or equivalent components and portions are denoted by the same reference signs. Moreover, dimensional ratios in the drawings may be exaggerated for convenience of description, and may be different from actual ratios. Furthermore, a function of each electrode mentioned below is merely an example, and a configuration of the present invention is not limited thereto.

In the following description, "upstream" and "downstream" are defined along a direction in which a liquid sample with which a sensor is spotted flows in a channel.

A measurement device of the present exemplary embodiment includes an insertion port into which a sensor is inserted, and plural terminals that contact the sensor inside the insertion port, wherein the terminals slide on a contact surface at which the sensor faces the terminals during a period from start of insertion to completion of insertion of the sensor, and a measurement target component contained in a liquid sample attached to the sensor is measured in a state in which the sensor is inserted into the insertion port.

The liquid sample is a sample in a liquid state subjected to measurement by the measurement device, and is, for example, a body fluid collected from a living body, and specifically, blood and urine are examples thereof. The measurement target component is a component that is contained in a liquid sample and can be quantitatively or qualitatively measured by the measurement device. In a case in which the liquid sample is blood, examples of the measurement target component include blood glucose, hemoglobin, and HbA1c. In a case in which the liquid sample is urine, examples of the measurement target component include urine sugar, bilirubin, and urinary protein. Hereinafter, an example of measuring a blood glucose level as a measurement target component for blood as a liquid sample will be described.

Here, in the sensor, a first electrode group located on a rear end side in an insertion direction and a second electrode group located on a farther distal end side as compared with the first electrode group are included on a contact surface that contact terminals in an insertion region that is a portion inserted into the insertion port.

In other words, when viewed from a side where the sensor is inserted into the measurement device, the first electrode group is located on the front side of the sensor, and the second electrode group is located on the rear side of the sensor. The first electrode group and the second electrode group can each be formed as an electrode layer formed from a metal material or a carbon material on a substrate formed on the contact surface of the sensor. Here, the first electrode group and the second electrode group are used for different purposes, and are preferably insulated from each other.

Moreover, in the measurement device, plural terminals receive normal forces from the contact surface by pressing the contact surface by stress generated by insertion of the insertion region of the sensor, for example, elastic deformation. Further, the plural terminals include a first terminal group that contacts the first electrode group on a side closer to the insertion port than a side on which a second terminal group that contacts the second electrode group. Furthermore, the sum of normal forces that the first terminal group receives from the contact surface of the sensor in a state in which the sensor is inserted into the insertion port is smaller than the sum of normal forces that the second terminal group receives from the contact surface of the sensor.

Each of the plural terminals can be formed from a metal material such as copper, brass, phosphor bronze, iron, or stainless steel, or a conductive material such as a carbon material, and is further subjected to surface treatment such as nickel plating, tin plating, chromium plating, palladium plating, or gold plating.

In a case in which the sensor is inserted, each of the plural terminals receives stress such as elastic deformation by the thickness of the sensor as compared with a state where the sensor is not inserted. The contact surface of the sensor is pressed by a restoring force of the stress, and the terminals receive normal forces from the contact surface as reaction forces.

The first terminal group contacts the first electrode group, and the second terminal group is in contact with the second electrode group in a state in which the sensor is inserted into the measurement device. In a case in which insertion of the sensor is started, the first terminal group first contacts the distal end of the sensor. The sensor is further inserted into the depth of the insertion port while the contact surface of the sensor slides on the first terminal group. Then, only immediately before insertion of the sensor is completed, the second terminal group contacts the distal end of the sensor. Therefore, the distance by which the first terminal group moves on the contact surface of the sensor is longer than the distance by which the second terminal group moves on the contact surface of the sensor.

Therefore, in order to reduce damage caused between the first terminal group that moves a longer distance on the contact surface of the sensor and the contact surface of the sensor, the sum of normal forces that the first terminal group receives from the contact surface of the sensor is made smaller than the sum of normal forces that the second terminal group receives from the contact surface of the sensor.

Note that the configuration for the difference in normal forces that the first terminal group and the second terminal group receive can be implemented by, for example, the deflection amount caused by insertion of the insertion region for each of the terminals of the first terminal group being made smaller than the deflection amount caused by insertion of the insertion region for each of the terminals of the second terminal group.

Further, it is preferable to configure such that each of the plural terminals includes a mounting base portion, an extending portion extending from the mounting base portion in a direction of the insertion port, and a contact portion bent in a direction in which the contact surface is located on the distal end side of the extending portion and in contact with the contact surface, and that extending portions of the terminals of the second terminal group are located closer to a side on which the contact surface is located as compared with extending portions of the terminals of the first terminal group. The configuration in which the deflection amount of the first terminal group is smaller than the deflection amount of the second terminal group as described above can be easily implemented by this configuration.

It is preferable for some of the terminals of the second terminal group to be bifurcated. With such a configuration, the sum of normal forces generated in the second terminal group can be increased while normal forces generated in the respective contact portions of the second terminal group is reduced.

FIG. 1 is a perspective view illustrating appearance of a measurement device 1 according to the present exemplary embodiment. As an example, the present exemplary embodiment is an example in which the measurement device 1 is a portable blood glucose level meter. In FIG. 1, a portable blood glucose level meter as a measurement device 1 and a sensor 2 configured to be detachable from the measurement device 1 are included. The sensor 2 is an example of a test tool of the disclosure. The sensor 2 includes a sample supply port **2*d* as an introduction port of a channel 2*a* to be described below for introducing a liquid sample (for example, blood of a patient) into the channel 2***a* and an air hole 2*e* for discharging air in the channel 2*a* due to introduction of the liquid sample, and is configured to include a function of detecting a measurement target component (for example, blood glucose) in the liquid sample. The measurement device 1 illustrated in FIG. 1 can be used in a state in which the sensor 2 is attached as a blood glucose meter that is, for example, a portable blood glucose meter, a blood glucose self measurement meter or the like, in a case in which the liquid sample is blood of a patient.

The measurement device 1 includes a main body 1*a*, and the main body 1*a* includes an insertion port 1*b* for inserting the strip-shaped sensor 2. Moreover, the main body 1*a* includes a voltage applicator (not illustrated) that supplies a predetermined voltage signal to the sensor 2, receives a current signal indicating a measurement result from the sensor 2, and performs A/D conversion. Moreover, the main body 1*a* includes a control unit (not illustrated) that is configured by, for example, a microprocessor and controls each unit of the measurement device 1. The control unit causes the sensor 2 to supply a predetermined voltage signal from the voltage applicator, and generates measurement data indicating a measurement value on the basis of a current value from the sensor 2 according to the supply of the voltage signal. Measurement data obtained by a measurement unit is recorded in a recording unit (not illustrated). The measurement data obtained by the control unit is recorded in the recording unit in association with measurement time, a patient ID, and the like.

Moreover, the main body 1*a* includes a display screen 1*c* for displaying measurement data and a connector 1*d* for performing data communication with an external device. The connector 1*d* transmits and receives data such as measurement data, measurement time, and a patient ID to and from a portable device such as a smartphone or a personal computer as an external device. That is, the measurement device 1 is configured to be able to transfer measurement data or measurement time to an external device, or receive a patient ID or the like from an external device via the connector 1*d*, and associate the patient ID or the like with the measurement data or the like.

In addition to the above description, for example, the control unit may be included at the end of the sensor 2, and the measurement data may be generated on the sensor 2 side. Moreover, the main body 1*a* of the measurement device 1 may include a user interface including an input unit such as a button or a touch panel for a user such as a patient to input data. Moreover, the display screen 1*c* or the recording unit is not necessarily included in the main body 1*a*, but may be included in an external device connectable to the main body 1*a*.

Figure 2A:
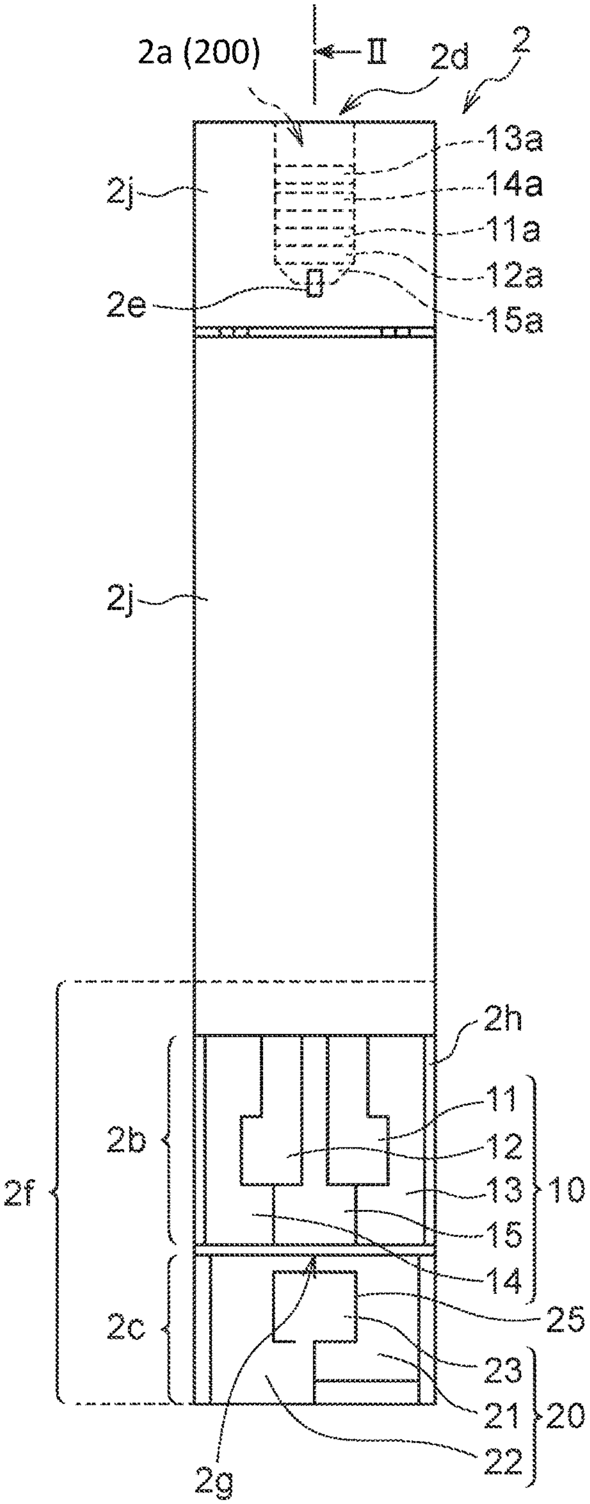
FIG. 2A is a plan view schematically illustrating a schematic configuration of a sensor.
Figure 2B:
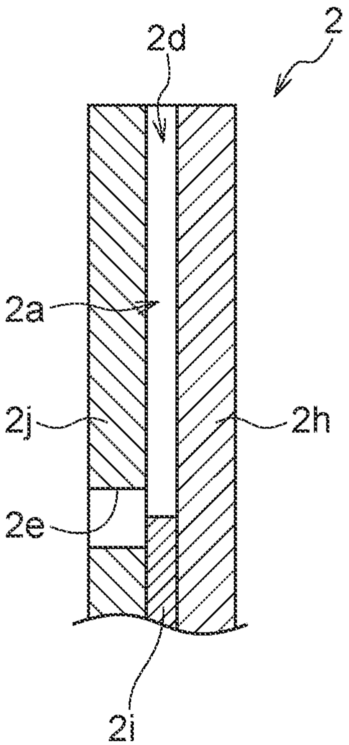
FIG. 2B is a cross-sectional view of an upstream portion viewed from a direction II in FIG. 2A.

FIG. 2A and FIG. 2B are a plan view (FIG. 2A) schematically illustrating the sensor 2 used in the measurement device 1 of the present exemplary embodiment and a cross-sectional view (FIG. 2B) of an upstream portion viewed from a direction II, respectively. In the figures, the upper side is the upstream side, and the lower side is the downstream side. In the sensor 2, for example, electrode layers formed using a metal material such as gold (Au) or a carbon material such as carbon are formed on a substrate 2*h* formed using a synthetic resin (plastic). On the electrode layers, a spacer 2*i* including a rectangular cutout portion as a covered region, and a synthetic resin cover 2*j* including the air hole 2*e* formed thereon are layered. A space including the sample supply port 2*d* formed by the cutout portion of the spacer 2*i* is formed by the layering of the substrate 2*h*, the spacer 2*i*, and the cover 2*j*, and this space serves as the channel 2*a*. The air hole 2*e* is formed in the vicinity of the downstream end of the channel 2*a*. The vicinity of the downstream end of the sensor 2 is a region where electrodes are exposed without being covered with the cover 2*j*, and is clearly divided into a first measurement region 2*b* on the upstream side and a second measurement region 2*c* on the downstream side. Moreover, a region to be inserted into the insertion port 1*b* of the measurement device 1 on the downstream end side of the sensor 2 is an insertion region 2*f*, and includes the lower end portion of the cover 2*j* in addition to the first measurement region 2*b* and the second measurement region 2*c*.

In the present exemplary embodiment, the electrode layers are formed as a first measurement electrode 11, a second measurement electrode 12, a third measurement electrode 13, a fourth measurement electrode 14, and a fifth measurement electrode 15 as a first electrode group 10, and a first reference electrode 21, a second reference electrode 22, and a third reference electrode 23 as a second electrode group 20.

The first electrode group 10 contains electrodes used for measuring a measurement target component contained in a liquid sample. The electrodes of the first electrode group 10 are each arranged in parallel in the longitudinal direction in the first measurement region 2*b*, and are the fourth measurement electrode 14, the second measurement electrode 12, the fifth measurement electrode 15, the first measurement electrode 11, and the third measurement electrode 13 from left to right in FIG. 2A. Note that the fourth measurement electrode 14, the fifth measurement electrode 15, and the third measurement electrode 13 all reach the downstream end of the first measurement region 2*b*, whereas the second measurement electrode 12 and the first measurement electrode 11 stop before the downstream end of the first measurement region 2*b*.

Each of the electrodes of the first electrode group 10 extends to the inside of the channel 2*a* on the upstream end side of the sensor 2 under the cover 2*j*, and is exposed in the channel 2*a* in parallel in a direction orthogonal to the longitudinal direction of the channel 2*a*. That is, a third spotting end 13*a*, a fourth spotting end 14*a*, a first spotting end 11*a*, a second spotting end 12*a*, and a fifth spotting end 15*a* are arranged in parallel from the upstream side in the channel 2*a*, and these are upstream ends of the third measurement electrode 13, the fourth measurement electrode 14, the first measurement electrode 11, the second measurement electrode 12, and the fifth measurement electrode 15, respectively. Note that adjacent electrodes are each insulated. For example, in a case in which the electrode layers are formed from a metal material formed by physical vapor deposition, the electrodes are each insulated by a predetermined electrode pattern being drawn using laser light (hereinafter referred to as "trimming"). Moreover, in the case of the electrode layers formed using a carbon material, each of the electrodes is formed at a predetermined interval.

On the downstream side of the first measurement region 2*b*, the second measurement region 2*c* insulated from the first measurement region 2*b* by trimming is included. In the second measurement region 2*c*, the second electrode group 20 is formed from a conductive material similarly to the electrode layers. The second electrode group 20 is electrodes not directly involved in measurement of a measurement target component but used for acquiring peripheral information such as lot or individual identification of the sensor 2, insertion detection of the sensor 2, or quality control.

The second electrode group 20 is divided into three regions, that is, the first reference electrode 21 on the right side, the second reference electrode 22 on the left side, and the substantially rectangular third reference electrode 23 at the center in FIG. 2A by a cutting line 25 trimmed using laser light. Note that, although the first reference electrode 21 and the second reference electrode 22 are separated by the cutting line 25 on the downstream side of the third reference electrode 23 and are not in direct conduction, they are in conduction on the upstream side. Moreover, the second reference electrode 22 and the third reference electrode 23 are in conduction on the left side of the downstream edge of the third reference electrode 23. The first reference electrode 21 and the third reference electrode 23 are separated by the cutting line 25 and are not in direct conduction.

Figure 3:
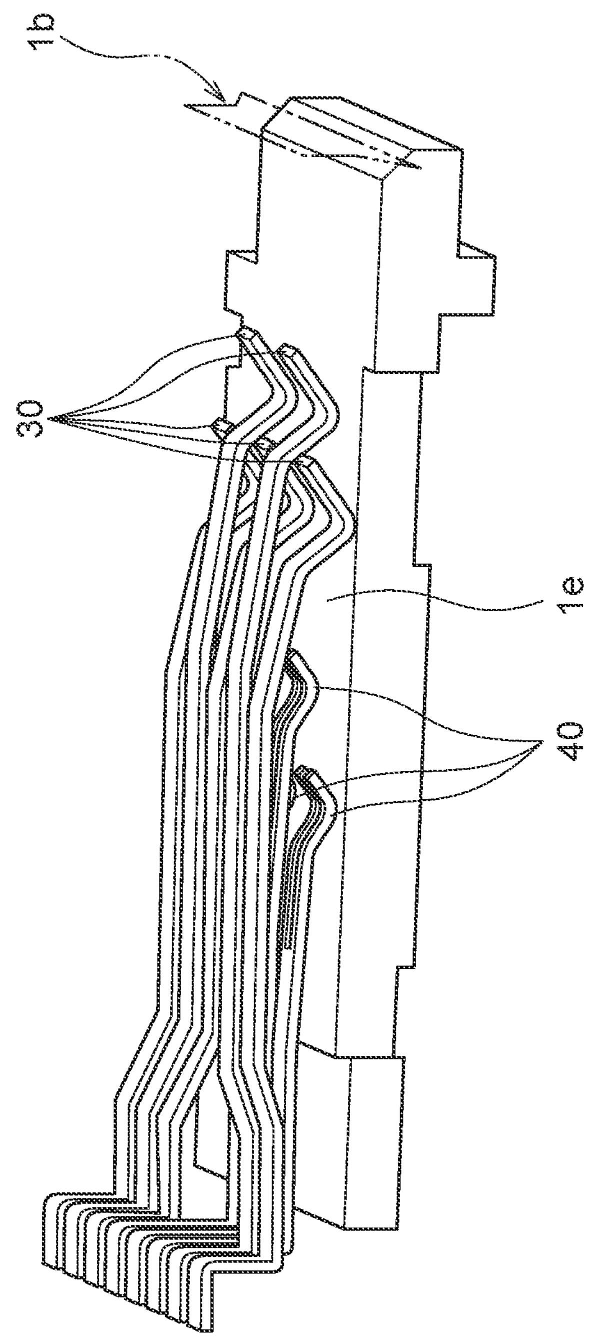
FIG. 3 is a perspective view schematically illustrating a schematic configuration of the shapes of terminals inside an insertion port of the measurement device.
Figure 4:
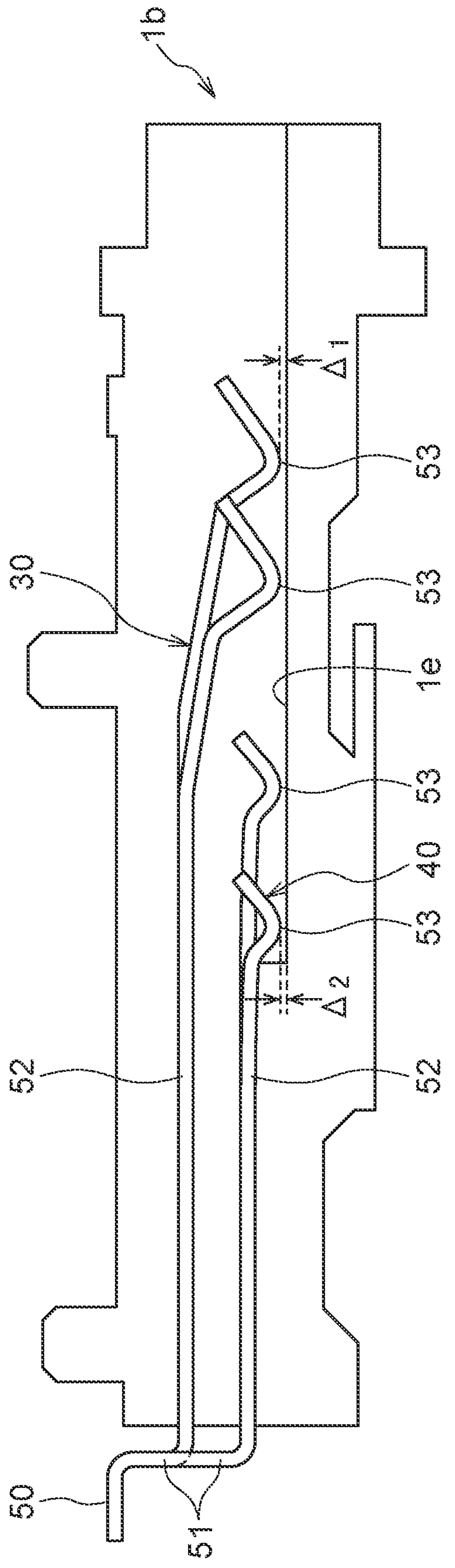
FIG. 4 is a side view schematically illustrating a schematic configuration of the shapes of the terminals of FIG. 3.

FIG. 3 is a perspective view illustrating a schematic configuration of the shapes of the terminals inside the insertion port 1*b* of the measurement device 1. Moreover, FIG. 4 is a side view schematically illustrating a schematic configuration of the shapes of the terminals of FIG. 3. A sensor support base 1*e* that supports the sensor 2 inserted from the insertion port 1*b* is included inside the measurement device 1. Further, above the sensor support base 1*e*, the plural terminals including mounting base portions 50 (see FIG. 4) on the rear side of the measurement device 1 and extending toward the insertion port 1*b* are located. Among the plural terminals, it is the first terminal group 30 that has distal ends extending closer to the insertion port 1*b*. Moreover, among the plural terminals, it is the second terminal group 40 that has distal ends located farther from the insertion port 1*b*. In other words, the distance from the insertion port 1*b* to the second terminal group 40 is longer than the distance from the insertion port 1*b* to the first terminal group 30.

As illustrated in FIG. 4, each of the first terminal group 30 and the second terminal group 40 includes the mounting base portions 50, bent portions 51 bent 90° from the mounting base portions 50 toward the sensor support base 1*e*, extending portions 52 extending from the lower ends of the bent portions 51 toward the insertion port 1*b* while keeping the distance from the sensor support base 1*e*, and contact portions 53 bent in a substantially V shape toward the sensor support base at the distal ends of the extending portions 52. In each of the first terminal group 30 and the second terminal group 40, a gap having a distance less than the thickness of the sensor 2 is kept between the contact portions 53 and the sensor support base 1*e* in a state in which the sensor 2 is not inserted. Moreover, the extending portions 52 of the terminals of the second terminal group 40 are located closer to the sensor support base 1*e* as compared with the extending portions 52 of the terminals of the first terminal group 30. Furthermore, each of a gap $\Delta_1$ between the contact portions 53 of the first terminal group 30 and the sensor support base 1*e* and a gap $\Delta_2$ between the contact portions 53 of the second terminal group 40 and the sensor support base 1*e* is shorter than the thickness T (see FIG. 8) of the first measurement region 2*b* and the second measurement region 2*c* of the sensor 2, and the gap $\Delta_1$ is longer than the gap $\Delta_2$.

Figure 5:
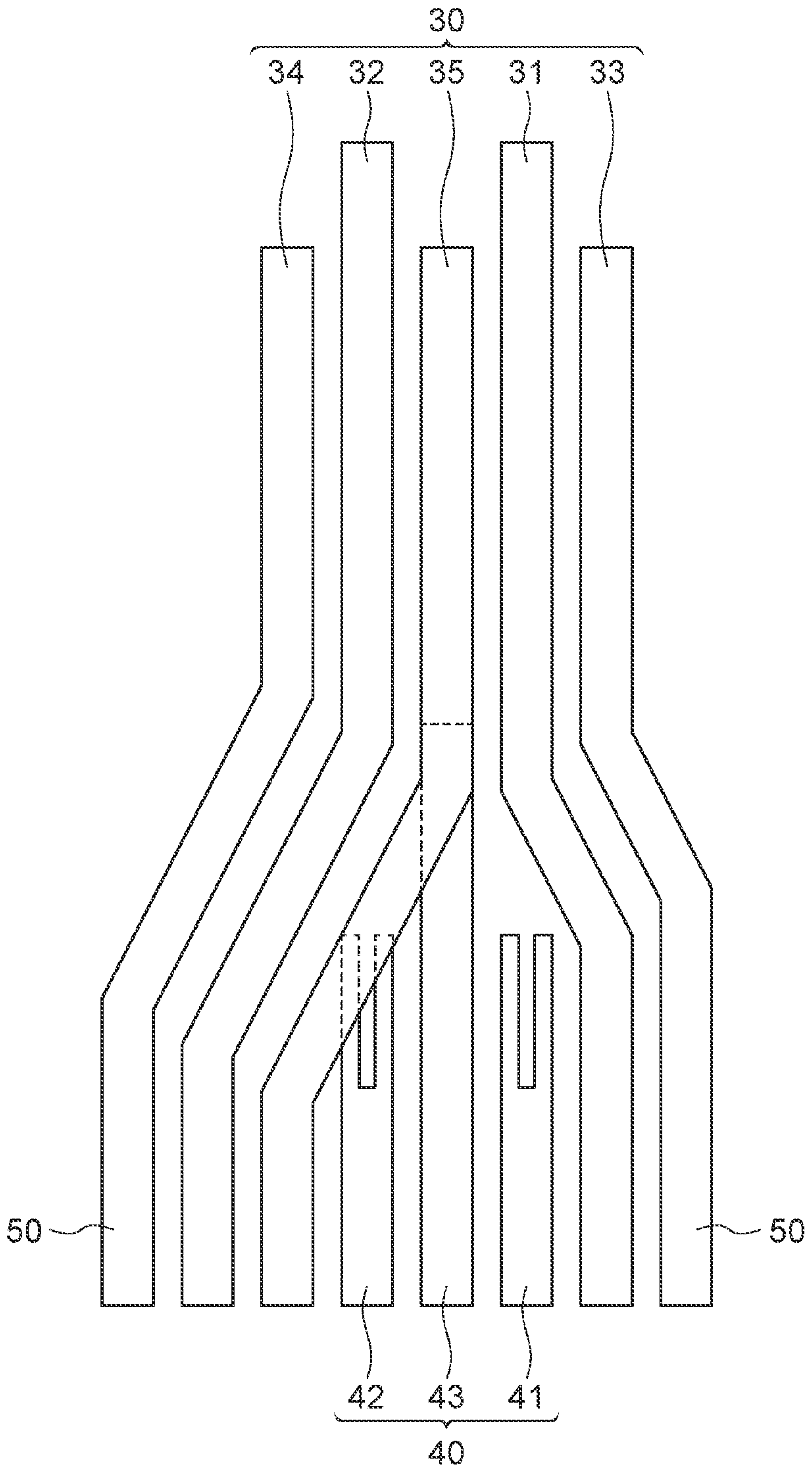
FIG. 5 is a plan view schematically illustrating the schematic configuration of the shapes of the terminals of FIG. 3.

FIG. 5 is a plan view schematically illustrating the schematic configuration of the shapes of the terminals of FIG. 3. In the drawing, the upper side indicates the insertion port 1*b* side. The first terminal group 30 includes a fourth measurement terminal 34, a second measurement terminal 32, a fifth measurement terminal 35, a first measurement terminal 31, and a third measurement terminal 33 from left to right in the drawing, and is configured to contact the fourth measurement electrode 14, the second measurement electrode 12, the fifth measurement electrode 15, the first measurement electrode 11, and the third measurement electrode 13 illustrated in FIG. 2A, respectively. The distal ends of the first measurement terminal 31 and the second measurement terminal 32 are located closer to the insertion port 1*b* as compared with the distal ends of the third measurement terminal 33, the fourth measurement terminal 34, and the fifth measurement terminal 35.

On the other hand, the second terminal group 40 includes a second reference terminal 42, a third reference terminal 43, and a first reference terminal 41 from left to right in the drawing, and is configured to contact the second reference electrode 22, the third reference electrode 23, and the first reference electrode 21 illustrated in FIG. 2A, respectively. The distal end of the third reference terminal 43 is located closer to the insertion port 1*b* as compared with the distal ends of the first reference terminal 41 and the second reference terminal 42. Moreover, in the second terminal group 40, the distal ends of the first reference terminal 41 and the second reference terminal 42 are bifurcated.

At the positions of the mounting base portions 50 located below the drawing of FIG. 5, the fourth measurement terminal 34, the second measurement terminal 32, and the fifth measurement terminal 35 of the first terminal group 30, the second reference terminal 42, the third reference terminal 43, and the first reference terminal 41 of the second terminal group 40, and further the first measurement terminal 31 and the third measurement terminal 33 of the first terminal group 30 are arranged in this order from left to right in the drawing. Then, the fourth measurement terminal 34, the second measurement terminal 32, and the fifth measurement terminal 35 of the first terminal group 30 extend toward the insertion port 1*b* while being shifted from the leftward position toward the center. On the other hand, the first measurement terminal 31 and the third measurement terminal 33 of the first terminal group 30 extend toward the insertion port 1*b* while being shifted from the rightward position toward the center. All three of the second terminal group 40 extend straight toward the insertion port 1*b*.

Figure 6:
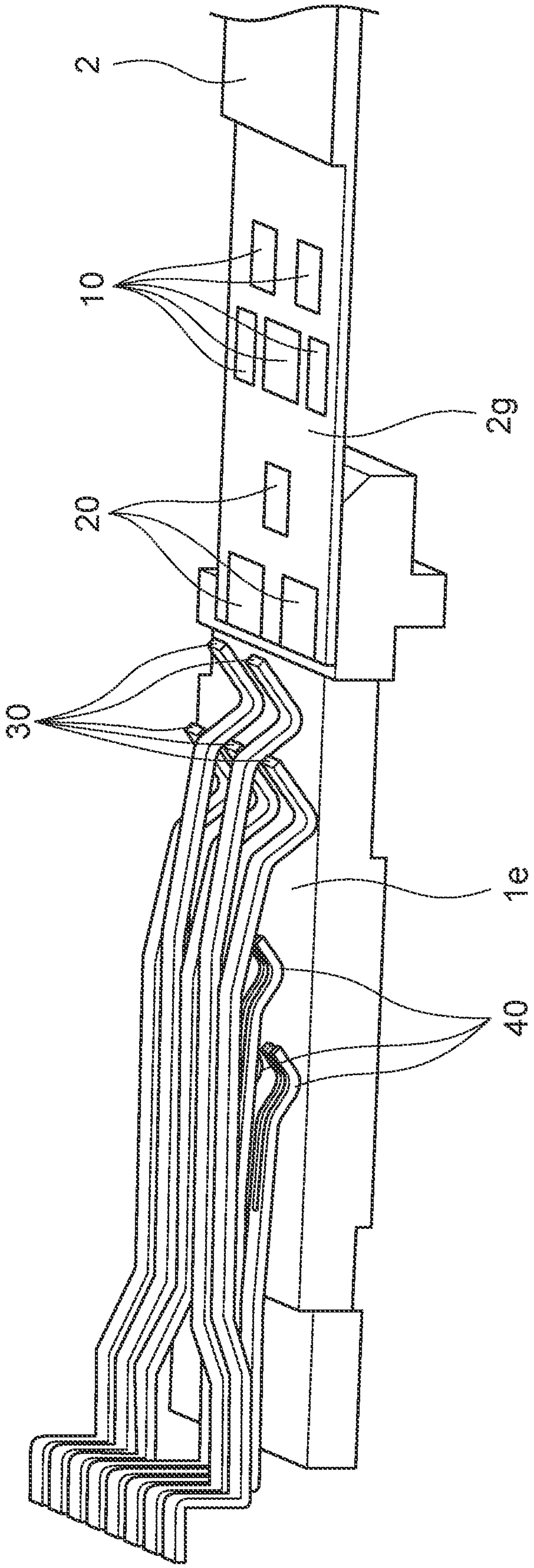
FIG. 6 is a perspective view schematically illustrating a state in which the sensor starts to be inserted into the measurement device.

FIG. 6 is a perspective view schematically illustrating a state in which the sensor 2 starts to be inserted into the measurement device 1. In a case in which the sensor 2 starts to be inserted into the measurement device 1, the second electrode group 20 among the electrodes on the contact surface 2*g* is first inserted into the insertion port 1*b*. Then, the distal end of the sensor 2 enters between the first terminal group 30 and the sensor support base 1*e* while the first terminal group 30 located on a side close to the insertion port 1*b* is deflected upward by elastic deformation. As the sensor 2 is further inserted, the first electrode group 10 enters the insertion port 1*b*. Then, the distal end of the sensor 2 enters between the second terminal group 40 and the sensor support base 1*e* while the second terminal group 40 located on a side far from the insertion port 1*b* is deflected upward by elastic deformation. The insertion of the sensor 2 into the insertion port 1*b* is completed in a case in which the first terminal group 30 contacts the first electrode group 10 and the second terminal group 40 contacts the second electrode group 20 at this time in this state as illustrated in the perspective view of FIG. 7 and the side view of FIG. 8.

Here, the distance $D_1$ by which terminals closest to the insertion port 1*b* (that is, first measurement terminal 31 and second measurement terminal 32, see FIG. 5) in the first terminal group 30 slide on the contact surface 2*g* is longer than the distance $D_2$ by which terminals farthest from the insertion port 1*b* (that is, first reference terminal 41 and second reference terminal 42, see FIG. 5) in the second terminal group 40 slide on the contact surface 2*g*. Then, the distance by which the sensor 2 deflects the contact portions 53 of the first terminal group 30, i.e., the deflection amount of the first terminal group 30 ($T-\Delta_1$) is smaller than the deflection amount ($T-\Delta_2$) of the second terminal group 40.

Figure 7:
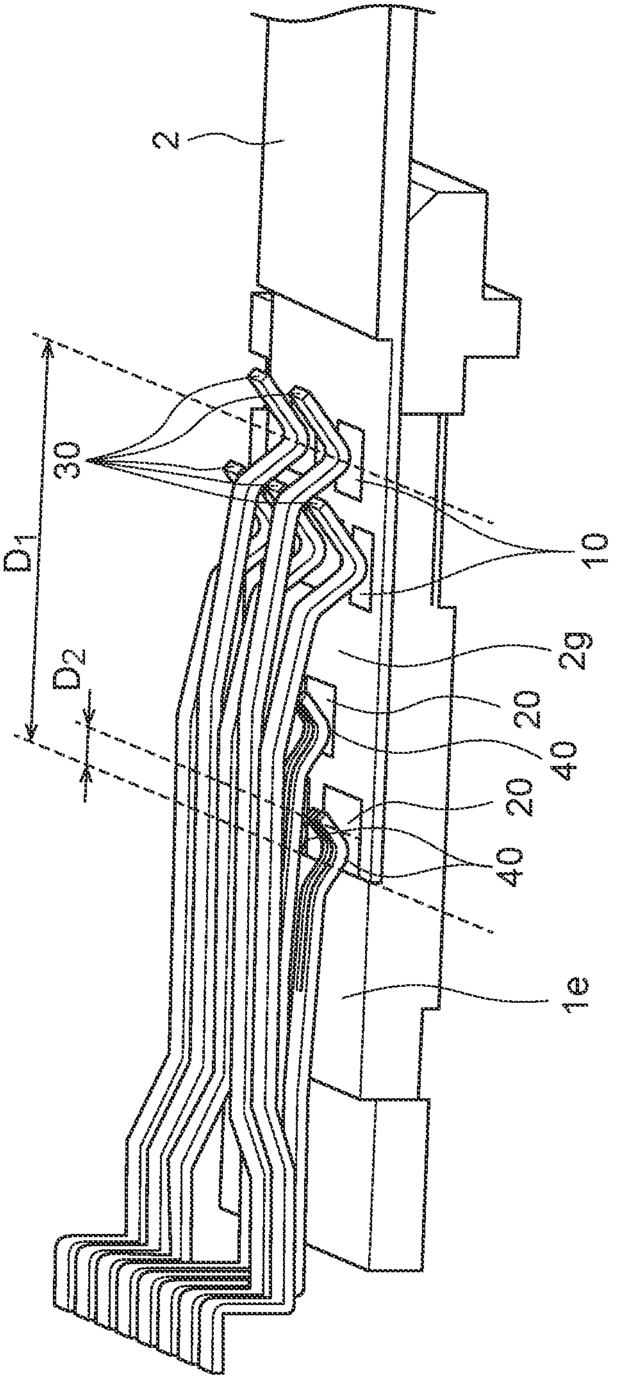
FIG. 7 is a perspective view schematically illustrating a state in which the sensor has been inserted into the measurement device.
Figure 8:
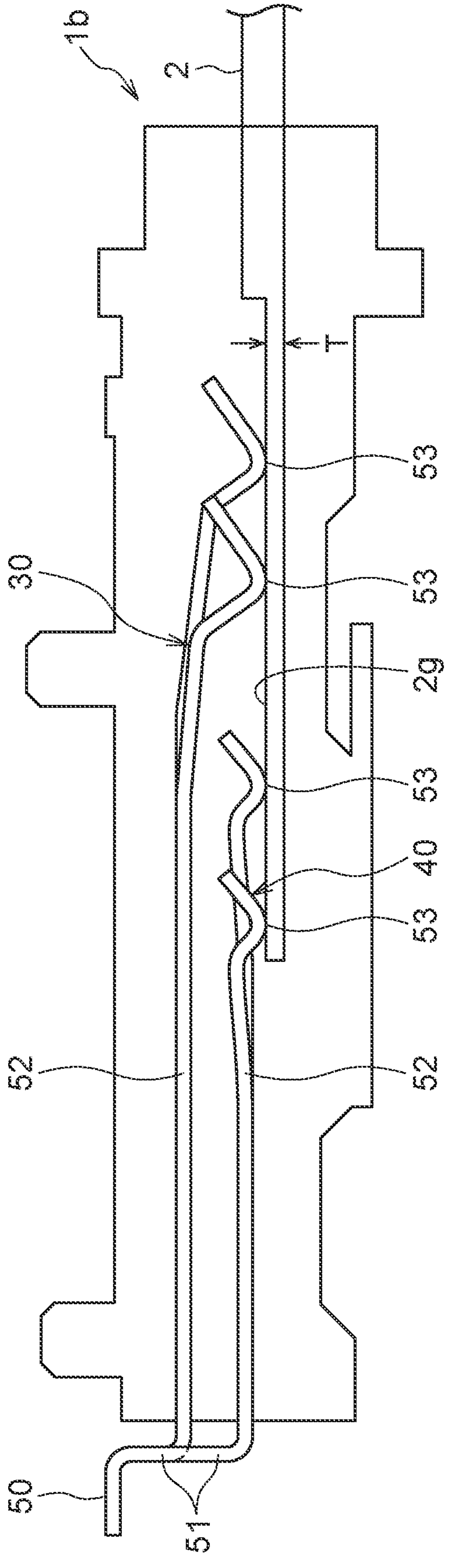
FIG. 8 illustrates the state of FIG. 7 in a side view.
Figure 9:
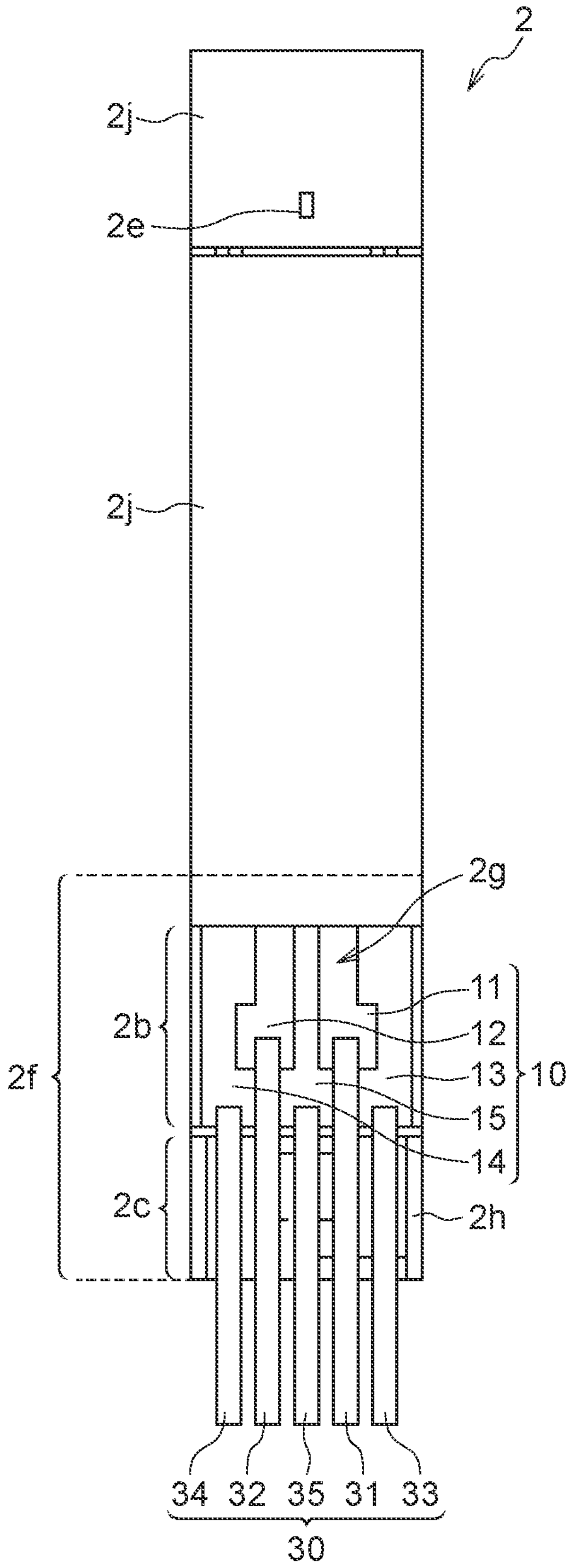
FIG. 9 is a plan view schematically illustrating a contact state between the sensor and a first terminal group.
Figure 10:
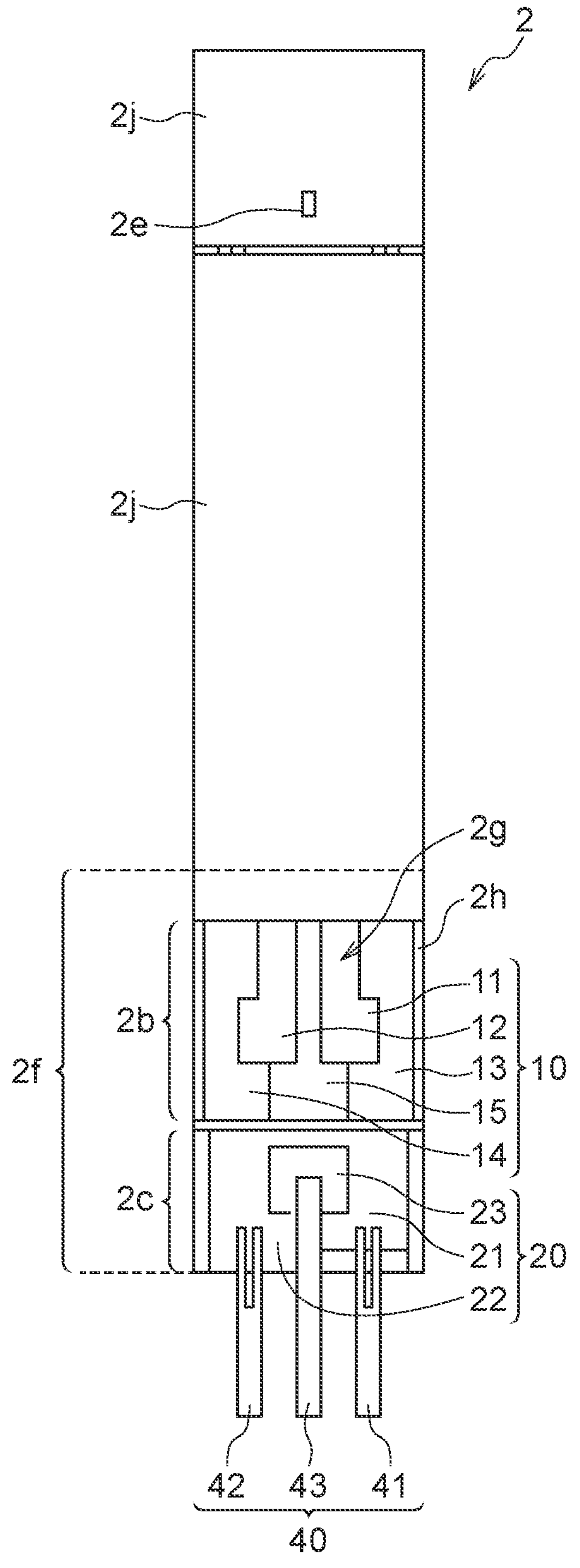
FIG. 10 is a plan view schematically illustrating a contact state between the sensor and a second terminal group.

FIGS. 9 and 10 are plan views of FIGS. 7 and 8 illustrating a state in which insertion of the sensor 2 is completed. Note that the second terminal group 40 is omitted in FIG. 9, and the first terminal group 30 is omitted in FIG. 10. In a state in which the sensor 2 is inserted into the measurement device 1, as illustrated in FIG. 9, the first measurement terminal 31 contacts the first measurement electrode 11, the second measurement terminal 32 contacts the second measurement electrode 12, the third measurement terminal 33 contacts the third measurement electrode 13, the fourth measurement terminal 34 contacts the fourth measurement electrode 14, and the fifth measurement terminal 35 contacts the fifth measurement electrode 15. At the same time, as illustrated in FIG. 10, the first reference terminal 41 contacts the first reference electrode 21, the second reference terminal 42 contacts the second reference electrode 22, and the third reference terminal 43 contacts the third reference electrode 23.

A measurement target component (for example, blood glucose) contained in blood as a liquid sample can be measured by the measurement device 1 into which the sensor 2 is inserted. Here, the content of a specific measurement target component can be measured by a reagent that reacts with the measurement target component being applied on the upstream side of any first electrode group 10 (for example, first spotting end 11*a*) involved in the measurement of the measurement target component and a potential difference caused by this sample dissolved by a liquid sample and reacting with the measurement target component being detected through the first terminal group 30. In a case in which the sample supply port 2*d* of the sensor 2 is spotted with blood in the example of the present exemplary embodiment, the blood flows downstream through the channel 2*a* by a capillary force while the third spotting end 13*a*, the fourth spotting end 14*a*, the first spotting end 11*a*, the second spotting end 12*a*, and the fifth spotting end 15*a* being immersed from the upstream side. Meanwhile, for example, a blood glucose level (that is, glucose concentration) is measured by the first measurement electrode 11 and the second measurement electrode 12, another index of blood (for example, hematocrit value) is measured by the third measurement electrode 13 and the fourth measurement electrode 14 located on the upstream side of the channel 2*a*, and whether the spotting amount of the blood to the channel 2*a* is sufficient is detected using the fifth measurement electrode 15 located on the most downstream side of the channel 2*a*. On the other hand, although the second electrode group 20 is not directly involved in measurement of a measurement target component, the second electrode group 20 is used for acquiring peripheral information such as individual identification of the sensor 2 or quality control. Note that the sensor 2 on which a liquid sample is spotted in advance may be inserted into the measurement device 1.

Here, each of the electrodes of the first terminal group 30 and the second terminal group 40 can be regarded as a cantilever beam using the mounting base portion 50 as a fulcrum as illustrated in FIG. 4. Then, providing that the length of each of the electrodes is L, a longitudinal elastic coefficient is E, a moment of inertia of area is I, and a force applied to the contact portion 53 is P, the deflection amount δ of the contact portion 53 is given by the following Formula (1).

$$\delta = (PL^3)/(3EI) \quad (1)$$

When Formula (1) is transformed for P, the following Formula (2) is derived.

$$P = (3EI/L^3)\cdot\delta \quad (2)$$

That is, in the same electrode, the force P is proportional to the deflection amount δ. Here, in a case in which the sensor 2 is inserted from the state illustrated in FIG. 4 and each of the electrodes is bent upward by the distance 6 as illustrated in FIG. 8, the contact portion 53 of each of the electrodes receives a normal force of the force P obtained by Formula (2) from the contact surface 2*g* of the sensor 2.

Here, assuming that the materials and the cross-sectional areas of the respective electrodes are the same, the deflection amount of the first terminal group 30 ($T-\Delta_1$) is smaller than the deflection amount of the second terminal group 40 ($T-\Delta_2$). Furthermore, since the first terminal group 30 is longer than the second terminal group 40, normal forces generated in the first terminal group 30 are smaller than normal forces generated in the second terminal group 40 according to Formula (2).

Figure 11:
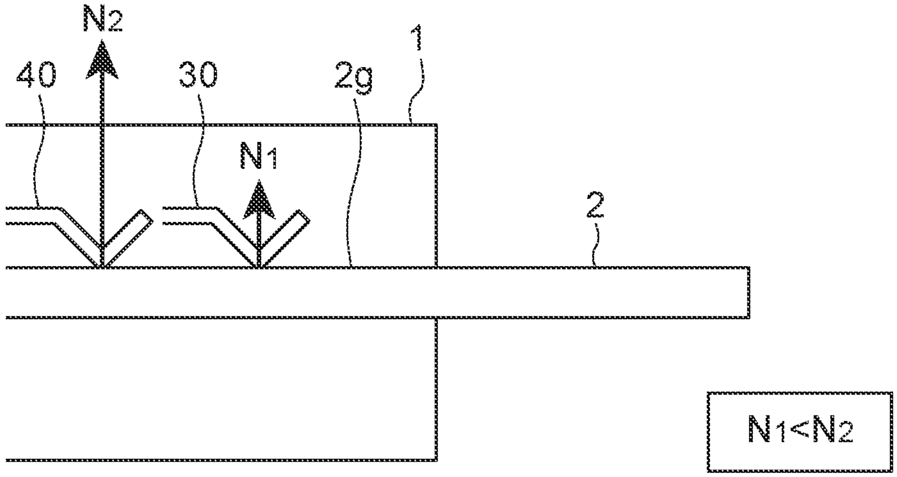
FIG. 11 schematically illustrates a relationship between normal forces that the terminals receive from a contact surface of the sensor and gravity generated in the sensor.

FIG. 11 schematically illustrates the measurement device 1 in a state in which the sensor 2 is attached. As illustrated in this drawing, the sum $N_1$ of the normal forces applied to the first terminal group 30 is smaller than the sum $N_2$ of the normal forces applied to the second terminal group 40.

Moreover, in the first terminal group 30 having normal forces smaller than those of the second terminal group 40, the sliding distance ($D_1$) on the contact surface 2*g* is longer than that of the second terminal group 40. Therefore, the possibility of surface damage of the contact surface 2*g* and the contact portions 53 due to sliding of the first terminal group 30 can be reduced. On the other hand, the influence of surface damage due to the normal forces of the second terminal group 40 is even smaller since the second terminal group 40 having larger normal forces has a shorter sliding distance ($D_2$) on the contact surface 2*g*. Note that, it is preferable to reduce a frictional force between the first terminal group 30 and the contact surface and the surface damage, by coating a part of a region where the first terminal group 30 slides (for example, surface between a portion of the third measurement terminal 33, the fourth measurement terminal 34, and the fifth measurement terminal 35 which the terminals contact, and a portion of the third reference terminal 43 which the terminal contacts) by using a substance that reduces a frictional force (for example, lubricating oil) or by performing surface treatment for reducing surface roughness in the contact surface 2*g*.

Since the first terminal group 30 having a longer sliding distance with respect to the contact surface 2*g* is arranged in the upper stage and the second terminal group 40 having a shorter sliding distance with respect to the contact surface 2*g* is arranged in the lower stage as illustrated in FIGS. 4 and 8, a spring elastic coefficient of the first terminal group 30 can be easily made lower than a spring elastic coefficient of the second terminal group 40. This configuration also contributes to making the normal forces applied to the first terminal group 30 smaller than the normal forces applied to the second terminal group 40.

Moreover, some of the second terminal group 40, specifically, the contact portions 53 of the first reference terminal 41 and the second reference terminal 42 have bifurcated distal ends as illustrated in FIG. 5. As a result, the sum of normal forces can be set to be constant even if the normal forces individually generated at the distal ends of the contact portions 53 are set to be smaller.

Note that, in the embodiment of the disclosure, the sum of normal forces generated in the terminals farthest from the insertion port 1*b* (specifically, first reference terminal 41 and second reference terminal 42) in the second terminal group 40 is preferably larger than the sum of normal forces generated in the terminals closest to the insertion port 1*b* (specifically, first measurement terminal 31 and second measurement terminal 32) in the first terminal group 30, and more preferably, the former is twice or more the latter.

EXAMPLES

(1) Example 1

In a sensor of Example 1, specifications of each of the terminals illustrated in FIG. 5 were set as indicated in Table 1 below. Note that the normal force indicates a value obtained by measuring a force required to deflect each of the terminals by the deflection amount listed in the following Table 1 using a force gauge (DPX-0.5T, IMADA) (the same applies to the following tables).

TABLE 1

| | Terminal | Width (mm) | Deflection amount (mm) | Normal force (N) | Sliding distance (mm) |
|---|---|---|---|---|---|
| First terminal group | First measurement terminal<br>Second measurement terminal | 0.4 | 0.15 | 0.2 | 6.00 |
| | Third measurement terminal<br>Fourth measurement terminal<br>Fifth measurement terminal | 0.4 | 0.15 | 0.2 | 4.60 |
| Second terminal group | Third reference terminal | 0.4 | 0.15 | 0.2 | 2.50 |
| | First reference terminal (two) | 0.3 | 0.2 | 0.4 | 0.95 |
| | Second reference terminal (two) | 0.3 | 0.2 | 0.4 | 0.85 |

Note that the numerical values of the first reference terminal and the second reference terminal in Table 1 are for each of the bifurcated distal ends. From Table 1, the sum of normal forces of the first terminal group was 1.0 N (=0.2 N*5), and the sum of normal forces of the second terminal group was 1.8 N (=0.2 N+0.4 N*4). Therefore, the sum of the normal forces of the first terminal group is smaller than the sum of the normal forces of the second terminal group.

Moreover, since the mass of the sensor is 0.1 g, the gravity G applied to the sensor is $9.8*10^{-4}$ N. Here, providing that a static friction coefficient of the contact surface is μ', since the sum of the normal forces of the first terminal group is 1.0 N as described above, a static frictional force $F_1$ generated between the first terminal group and the contact surface is 1.0μ' (N). Similarly, since the sum of the normal forces of the second terminal group is 1.8 N as described above, a static frictional force $F_2$ generated between the second terminal group and the contact surface is 1.8μ' (N). Then, the static friction coefficient μ' is preferably set to be $F_1<G$ and $F_2>G$, in other words, preferably set in a numerical range of the following Formula (3).

$$5.4*10^{-4}<\mu'<9.8*10^{-4} \tag{3}$$

(2) Example 2

In a sensor of Example 2, specifications of each of the terminals illustrated in FIG. 5 were set as indicated in Table 2 below.

TABLE 2

| | Terminal | Width (mm) | Deflection amount (mm) | Normal force (N) | Sliding distance (mm) |
|---|---|---|---|---|---|
| First terminal group | First measurement terminal<br>Second measurement terminal | 0.4 | 0.2 | 0.2 | 6.00 |
| | Third measurement terminal<br>Fourth measurement terminal<br>Fifth measurement terminal | 0.4 | 0.2 | 0.2 | 4.50 |
| Second terminal group | Third reference terminal | 0.4 | 0.2 | 0.2 | 2.50 |
| | First reference terminal (two) | 0.4 | 0.2 | 0.8 | 1.00 |
| | Second reference terminal (two) | 0.4 | 0.2 | 0.8 | 1.00 |

In the present example, the sum (0.8 N*4=3.2 N) of the normal forces of the terminals farthest from the insertion port and have the shortest moving distance on the contact surface (i.e., first reference terminal and second reference terminal) is larger than the sum (0.2 N*2=0.4 N) of the normal forces of the terminals closest to the insertion port and have the shortest moving distance on the contact surface (i.e., first measurement terminal and second measurement terminal), and specifically, is twice or more.

(3) Example 3

As the simplest way, the first terminal group can be set to four terminals having the same moving distance on the contact surface, and the second terminal group can also be set to four terminals having the same moving distance on the contact surface in specifications indicated in the following Table 3.

TABLE 3

| Terminal | Width (mm) | Deflection amount (mm) | Normal force (N) | Sliding distance (mm) |
|---|---|---|---|---|
| First terminal group (four) | 0.3 | 0.15 | 0.3 | 5.00 |
| Second terminal group (four) | 0.4 | 0.2 | 0.6 | 2.00 |

That is, in the present example, the sum of the normal forces of the second terminal group (0.6 N*4=2.4 N) is twice the sum of the normal forces of the first terminal group (0.3 N*4=1.2 N).

INDUSTRIAL APPLICABILITY

The present invention can be used in a measurement device in which a sensor is attached and a measurement target component contained in a liquid sample is measured.

What is claimed is:

1. A measurement device for measuring a target component contained in a liquid sample held in a sensor that is insertable into the measurement device in an insertion direction, the measurement device comprising:
- an insertion port into which an insert portion of the sensor is insertable, the insertion portion of the sensor being located at one side of opposing sides of the sensor with respect to the insertion direction and having a contact surface, the insertion portion including
- a first electrode group having a plurality of first electrodes disposed on the contact surface at positions closer to the other side of the opposing sides of the sensor than to the one side,
- a second electrode group having a plurality of second electrodes disposed on the contact surface at positions closer to the one side than to the other side; and
- a first terminal group including a plurality of first terminals respectively extending in the insertion direction in the insertion port and directly contacting the plurality of first electrodes of the first electrode group, the plurality of the first terminals respectively receiving normal forces from the contact surface via the plurality of first electrodes, and
- a second terminal group including a plurality of second terminals respectively extending in the insertion direction in the insertion port and directly contacting the plurality of second electrodes of the second electrode group, the plurality of the second terminals respectively receiving normal forces from the contact surface via the plurality of second electrodes, wherein
- a sum of normal forces received by the first terminal group is smaller than a sum of normal forces received by the second terminal group, wherein
- the insertion port has a support surface that contacts a bottom surface of the insertion portion opposite to the contact surface when the insertion portion is inserted, and
- the plurality of first terminals are respectively spaced apart from the support surface to have first gaps, and the plurality of second terminals are respectively spaced apart from the support surface to have second gaps in a direction orthogonal to the support surface.

2. The measurement device according to claim 1, wherein
- a sum of the first gaps of the plurality of first terminals is smaller than a sum of the second gaps of the plurality of second terminals.

3. The measurement device according to claim 2, wherein:
- each of the plurality of first terminals and the plurality of second terminals includes:
- a mounting base portion located on a side opposite to a side where the insertion port is located with respect to the insertion direction;
- an extending portion extending from the mounting base portion in the insertion direction; and
- a contact portion located within the insertion port and being bent in a direction away from the support surface of the insertion port, and
- the extending portion of each second terminal is located closer to the support surface of the insertion port than is the extending portion of each first terminal.

4. The measurement device according to claim 1,
- wherein at least one second terminal is branched to have a plurality of contact portions bent in the direction away from the sensor when the sensor is inserted into the insertion port.

5. The measurement device according to claim 1, wherein a normal force received by each of the plurality of first terminals is equal to or smaller than a normal force received by any one of the plurality of second terminals.

6. The measurement device according to claim 1, wherein each first gap is equal to or less than any one of the second gaps.

7. The measurement device according to claim 1, wherein a length of each first terminal is greater than a length of any one of the plurality of second terminals in the insertion direction.

8. The measurement device according to claim 1, wherein each of the plurality of first terminals and the plurality of second terminals is formed as a flat spring.

9. The measurement device according to claim 1, wherein the insertion port has a shape such that the sensor having a flat strip shape is insertable.

10. The measurement device according to claim 1, wherein the sensor is a biosensor.

11. The measurement device according to claim 1, wherein the liquid sample is a blood of a user, and the target component is a blood glucose level.

12. The measurement device according to claim 1, wherein the measurement device is a portable blood glucose measurement device.

* * * * *